United States Patent [19]

Fray

[11] Patent Number: 5,096,552
[45] Date of Patent: Mar. 17, 1992

[54] MONITORING OF PYROMETALLURGICAL PROCESSES

[75] Inventor: Derek J. Fray, Cambridge, Great Britain

[73] Assignee: Mineral Industry Research Organisation, London, Great Britain

[21] Appl. No.: 446,453

[22] Filed: Dec. 5, 1989

[30] Foreign Application Priority Data

Dec. 6, 1988 [GB] United Kingdom ............... 8828431

[51] Int. Cl.$^5$ ................. G01N 33/20; G01N 27/00
[52] U.S. Cl. ..................... 204/153.1; 204/153.15; 204/422; 204/423; 204/421; 204/406
[58] Field of Search ............... 204/422, 423, 421, 406, 204/153.15, 153.1

[56] References Cited

U.S. PATENT DOCUMENTS

| 3,413,150 | 11/1968 | Kummer et al. | 429/104 X |
|---|---|---|---|
| 3,672,995 | 6/1972 | Brown et al. | 429/104 |
| 3,829,331 | 8/1974 | Tsang | 429/104 |
| 3,877,995 | 4/1975 | Levine et al. | 429/104 |
| 3,878,059 | 4/1975 | Wechter et al. | 204/153.15 |
| 3,953,228 | 4/1976 | Roth et al. | 429/193 |
| 4,049,885 | 9/1977 | Mitoff | 429/104 |
| 4,055,710 | 10/1977 | May et al. | 429/104 |
| 4,166,009 | 8/1979 | Fray | 204/1 T |
| 4,166,209 | 8/1979 | Fray . | |
| 4,174,258 | 11/1979 | Bode | 204/195 S |
| 4,182,667 | 1/1980 | Dobson et al. | 204/153.15 X |
| 4,225,395 | 9/1980 | Tsang | 204/153.15 |
| 4,377,460 | 3/1983 | Hirayama et al. | 204/195 S |
| 4,406,754 | 9/1983 | Narita et al. | 204/1 T |
| 4,427,525 | 1/1984 | Lin et al. | 204/427 |
| 4,645,571 | 2/1987 | Dubreuil et al. | 204/1 T |
| 4,828,671 | 5/1989 | Lin et al. | 204/412 |
| 4,842,698 | 6/1989 | Kirchnerova et al. | 204/1 T |
| 4,855,034 | 8/1989 | Sugimoto et al. | 204/427 |

FOREIGN PATENT DOCUMENTS

| 1216895 | 1/1987 | Canada . |
|---|---|---|
| 0087322A1 | 8/1983 | European Pat. Off. . |
| A1-0208072 | 1/1987 | European Pat. Off. . |
| A2202596 | 4/1974 | France . |
| WO84/03149A | 1/1984 | PCT Int'l Appl. . |
| 1415416 | 11/1975 | United Kingdom . |
| 1470558 | 4/1977 | United Kingdom . |
| 2097538A | 11/1982 | United Kingdom . |
| 2109782A | 6/1983 | United Kingdom . |
| 2167867A | 6/1986 | United Kingdom . |

Primary Examiner—John Niebling
Assistant Examiner—Arun S. Phasge
Attorney, Agent, or Firm—Fleit, Jacobson, Cohn, Price, Holman & Stern

[57] ABSTRACT

The concentration of an element in a molten metallurgical phase (3) is measured by applying an electrical potential across two electrodes (1, 2) separated by a solid electrolyte (7) containing cations of the element to be measured immersed in the melt, and measuring the current flowing between them. The solid electrolyte is preferably of $\beta$-alumina or zirconium silicate or phosphate.

5 Claims, 1 Drawing Sheet

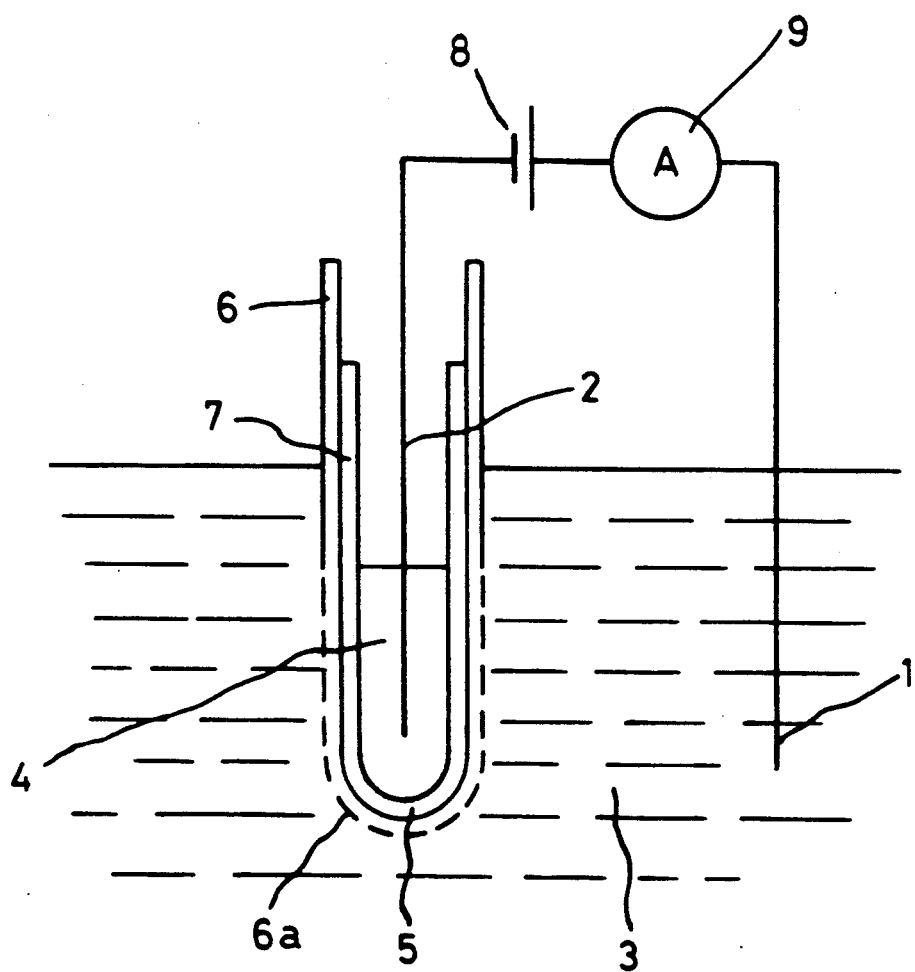

MONITORING OF PYROMETALLURGICAL PROCESSES

BACKGROUND OF THE INVENTION

This invention relates to the monitoring of pyrometallurgical processes, and more particularly to the measurement of concentrations of major metallic species in molten metallurgical phases such as slags, mattes, bullions and impure or semi-refined molten metals.

It is already known to use electrolytic sensors in which a reference electrode is separated by a solid electrolyte from an electrode immersed in a melt and an e.m.f. is measured, to study the concentration trend of a minor element in the melt. Such a procedure is described for example in UK patent no. GB-A-1,470,558, which corresponds to U.S. Pat. No. 4,166,009.

One of the disadvantages associated with the use of such sensors is that the e.m.f. change is the same for a change from 1 part per million to 10 parts per million of the element being detected as it is for the change from 10,000 to 100,000 p.p.m. Such devices are therefore considerably less sensitive at higher concentrations of the element being detected.

BRIEF SUMMARY OF THE INVENTION

It is an object of this invention to provide a method of monitoring the concentration of elements in metallurgical melts that is appreciably more sensitive to changes in concentration than the method described above.

Thus in one aspect the present invention provides a method of measuring the concentration of an element in a molten metallurgical phase, which comprises immersing in said phase two electrical leads which are separated by a solid electrolyte containing cations of the element to be measured, applying an electrical potential across the electrical leads and measuring the current flowing between them as a measure of concentration of the element in the molten phase.

Preferably the solid electrolyte is oxidic in character.

More preferably the solid electrolyte is based on $\beta$-alumina or zirconium silicate or phosphate, with a mobile cation which is a cation of the element to be measured incorporated therein.

The molten metallurgical phase is suitably a matte or impure molten metal.

Preferably the solid electrolyte is in the form of a tube surrounded by means adapted to create a stagnant layer of melt around the electrolyte.

The solid electrolyte should suitably be modified by partial substitution of its cationic content by cations of the element being detected, e.g. by means of immersion or electro-chemical exchange. Such a procedure is described in TRANS IMM.88 (1979) C229-233.

The invention in another aspect provides apparatus for measuring the concentration of an element in a melt comprising two electrical leads separated by a solid electrolyte made of $\beta$-alumina or zirconium silicate or zirconium phosphate containing cations of the element to be measured, a source of electrical potential to be applied across the electrical leads, and means for measuring current flowing between the electrical leads.

BRIEF DESCRIPTION OF THE DRAWING

The invention will be further described by way of example only, with reference to the accompanying drawing which shows in diagrammatic form an apparatus suitable for monitoring the copper content of a copper matte i.e. an impure metallic sulfide mixture produced by smelting the sulfide are of Cu.

DETAILED DESCRIPTION

As shown in the drawing, two electrical leads 1 and 2 are used. Lead 1 is immersed directly in a molten matte 3 while lead 2 is in contact with copper 4 enclosed within a closed-ended tube 5 composed of layers of porous refractory (alumina) which is penetrated by the molten matte (as indicated by numeral 6a) and copper-substituted $\beta$-alumina, designated 6 and 7 respectively. An electrical potential is applied across leads 1 and 2 by means of battery or cell 8 and the current flow is monitored by means of ammeter 9. The current flowing is directly proportional to the diffusional flux of copper from within the matte to the surface of the solid electrolyte 7 through the matte held in the porous membrane, and therefore linearly dependent on the concentration of copper in the molten matte. The copper 4 provides good electrical contact between the lead 2 and the solid electrolyte 7.

The invention will be further illustrated with reference to the following experimental procedure.

Molten lead and molten sodium were separated by a closed-ended ceramic tube made of $Na^+/\beta$-alumina. Iron wire electrical leads were inserted into the molten lead (negative) and the molten sodium (positive). These wires were connected via a source of e.m.f., an ammeter and a voltmeter. Sodium was titrated through the ceramic tube into the lead and from the coulombs passed the concentration of sodium in lead was calculated.

After each titration the system was allowed to equilibrate. A constant potential of 1 volt was then applied in the opposite direction so that sodium was transferred from the molten lead to the sodium reservoir. In this case the rate of transfer of sodium was controlled by diffusion of the sodium through the lead to the lead/$\beta$-alumina interface. As is shown in the following table the current, i.e. the rate of transfer of sodium, is a linear function of sodium concentration.

| APPLIED VOLTAGE (v) | CONCENTRATION (wt %) Na in Pb | CURRENT FLOWING (ma) |
|---|---|---|
| 1.03 | 1.22 | 0.18 |
| 1.03 | 2.45 | 0.232 |
| 1.027 | 3.67 | 0.263 |
| 1.02 | 4.90 | 0.300 |

It should be noted that in this experiment the melt was stagnant. However in an agitated or mobile system a porous layer around the $\beta$-alumina tube would be required in order to ensure a stagnant layer around the probe. Alternatively the probe may comprise a pellet of the solid electrolyte sealed into a ceramic tube some distance from the end thereof so as to create a stagnant zone at the bottom of the tube.

I claim:

1. A method of measuring the concentration of a metal included in a molten metallurgical phase selected from the group consisting of slags, mattes, bullions, impure molten metals, semi-refined molten metals and alloys thereof, comprising:

inserting two electrical leads into said molten phase so that each electrical lead is in electrical contact with said molten phase;

interposing between said electrical leads a layer of solid electrolyte containing cations of the metal to be measured;

providing a layer of material on said solid electrolyte to produce a stagnant layer of constant thickness of said molten phase in electrical contact with said layer of solid electrolyte;

applying an electrical potential across said electrical leads; and measuring the current flowing between said electrical leads as a measure of the concentration of said metal in said molten phase.

2. The method as claimed in claim 1, wherein:

said solid electrolyte comprises a material selected from the group consisting of $\beta$-alumina, zirconium silicate and zirconium phosphate, with a mobile cation of the metal to be measured included in said electrolyte.

3. The method as claimed in claim 1 wherein:

said metal is copper; and said molten phase is a copper matte.

4. Apparatus for measuring the concentration of a metal included in a molten metallurgical phase comprising:

two electrical leads in said molten phase in electrical contact with said phase;

a solid electrolyte interposed between said electrical leads and made of a material selected from the group consisting of $\beta$-alumina, zirconium silicate and zirconium phosphate and containing cations of the metal to be measured;

a layer of material on said solid electrolyte for creating a stagnant layer of said molten metallurgical phase adjacent said solid electrolyte;

a source of electrical potential connected across said electrical leads; and means for measuring current flowing between said electrical leads.

5. The apparatus as claimed in claim 4 wherein:

said metal is copper; and said molten phase is a copper matte.

* * * * *